(12) United States Patent
Fritsch et al.

(10) Patent No.: US 9,963,414 B2
(45) Date of Patent: May 8, 2018

(54) PROCESS FOR THE PREPARATION AND ISOLATION OF CARBOXYLIC ESTERS

(71) Applicants: ThyssenKrupp Industrial Solutions AG, Essen (DE); ThyssenKrupp AG, Essen (DE)

(72) Inventors: Markus Fritsch, Leipzig (DE); Armin Börner, Rostock (DE); Ivan Shuklov, Rostock (DE); Zeljko Knez, Maribor (SI)

(73) Assignees: THYSSENKRUPP INDUSTRIAL SOLUTIONS AG, Essen (DE); THYSSENKRUPP AG, Essen (DE)

( * ) Notice: Subject to any disclaimer, the term of this patent is extended or adjusted under 35 U.S.C. 154(b) by 0 days. days.

(21) Appl. No.: 15/101,899

(22) PCT Filed: Dec. 5, 2014

(86) PCT No.: PCT/EP2014/003254
§ 371 (c)(1),
(2) Date: Jun. 3, 2016

(87) PCT Pub. No.: WO2015/082077
PCT Pub. Date: Jun. 11, 2015

(65) Prior Publication Data
US 2016/0311748 A1    Oct. 27, 2016

(30) Foreign Application Priority Data
Dec. 6, 2013 (DE) ........................ 10 2013 225 215

(51) Int. Cl.
| C07C 51/02 | (2006.01) |
| C07C 51/42 | (2006.01) |
| C07C 67/08 | (2006.01) |
| C07C 51/09 | (2006.01) |
| C07C 51/43 | (2006.01) |
| C07C 51/493 | (2006.01) |
| C12P 7/62 | (2006.01) |
| C07C 67/54 | (2006.01) |
| C07C 67/56 | (2006.01) |

(52) U.S. Cl.
CPC ............ *C07C 51/42* (2013.01); *C07C 51/02* (2013.01); *C07C 51/09* (2013.01); *C07C 51/43* (2013.01); *C07C 51/493* (2013.01); *C07C 67/08* (2013.01); *C07C 67/54* (2013.01); *C07C 67/56* (2013.01); *C12P 7/62* (2013.01)

(58) Field of Classification Search
CPC .................................................. C07C 51/493
See application file for complete search history.

(56) References Cited

U.S. PATENT DOCUMENTS

| 8,674,131 | B2 * | 3/2014 | Barve .......................... 560/179 |
| 9,464,026 | B2 * | 10/2016 | Stensrud ............... C07C 29/149 |
| 2005/0070738 | A1 | 3/2005 | Isotani |
| 2009/0234160 | A1 | 9/2009 | Fujita et al. |
| 2011/0245515 | A1 | 10/2011 | Fruchey et al. |
| 2011/0275851 | A1 | 11/2011 | Orjuela et al. |
| 2014/0069299 | A1 | 3/2014 | Becker et al. |
| 2017/0015643 | A1 * | 1/2017 | Venkitasubramanian C07D 307/68 |

FOREIGN PATENT DOCUMENTS

| CN | 102731302 A | 10/2012 |
| DE | 69821951 T2 | 12/2004 |
| DE | 102007063507 A1 | 7/2009 |
| DE | 102011006557 A1 | 10/2012 |
| EP | 1005562 B1 | 2/2004 |
| EP | 3077359 A | 10/2016 |
| JP | 2005132836 A | 5/2005 |
| WO | 2015082077 A | 6/2015 |

OTHER PUBLICATIONS

Barve P. et al. Preparation of Pure Methyl Esters from Corresponding Alkali Metal Salts of Carboxylic Acids Using Carbon Dioxide and Methanol. Industrial and Engineering Chemistry Research 51(4)1498-1505, Feb. 1, 2012.*
English language machine translation of DE 10 2007 063 507 A1.
XP002735589, Database WPI, Week 200540, Thomson Scientific, London, AN 2005-389773.
XP002735590, Database Caplus [Online] Chemical Abstracts Service, Columbus, Ohio, US; Database accession No. 2012:1531268.

* cited by examiner

*Primary Examiner* — Ralph J Gitomer
(74) *Attorney, Agent, or Firm* — thyssenkrupp North America, Inc.

(57) ABSTRACT

The disclosed methods for preparing and isolating carboxylic esters ensure a high product purity and minimize technical complexity. These methods are based on the reaction of a carboxylic acid with an alcohol in an aqueous medium. In some examples, the alcohol is used both for the esterification and for the precipitation of the salts, preferably ammonium salts, formed in the synthesis.

22 Claims, 1 Drawing Sheet

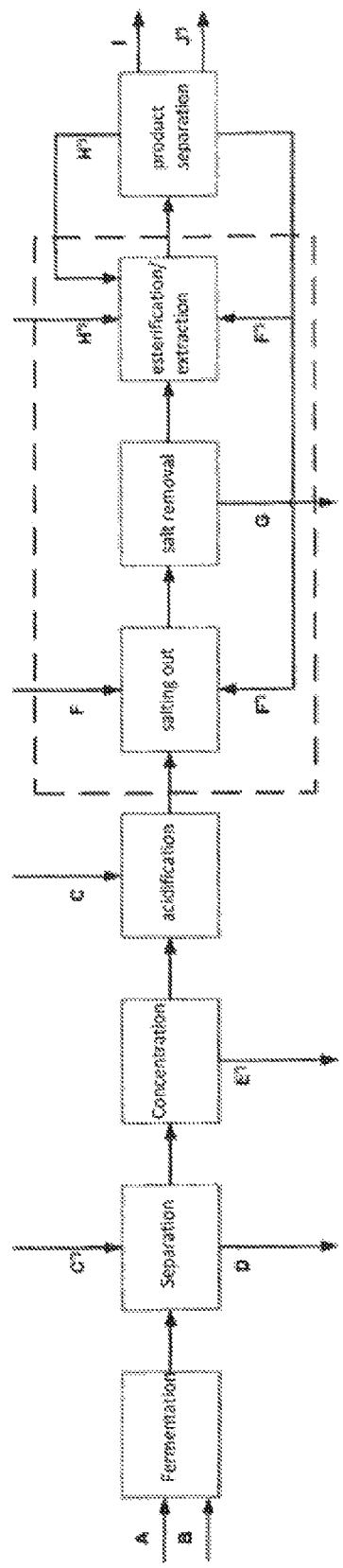

PROCESS FOR THE PREPARATION AND ISOLATION OF CARBOXYLIC ESTERS

CROSS REFERENCE TO RELATED APPLICATIONS

This application is a U.S. National Stage Entry of International Patent Application Serial Number PCT/EP2014/003254, filed Dec. 5, 2014, which claims priority to German Patent Application No. DE 102013225215.3 filed Dec. 6, 2013, the entire contents of both of which are incorporated herein by reference.

FIELD

The present disclosure relates to carboxylic esters and, more particularly, to methods for preparing and isolating carboxylic esters.

BACKGROUND

Various methods for preparing carboxylic acids by fermentation processes are known from the prior art, e.g. for succinic acid, lactic acid or citric acid. For optimal process conditions in the fermenter, the pH of the fermentation broth is adjusted by addition of a base (e.g. ammonium hydroxide, ammonium bicarbonate, sodium hydroxide, calcium hydroxide, etc.). Depending on the pH, this leads to the formation of a carboxylic acid salt, e.g. diammonium succinate in the case of neutralization of succinic acid with an ammonium base, or a mixture of carboxylic acid and salt.

The conversion of carboxylic acid salts to the free carboxylic acid again, e.g. by electrodialysis, is known from the prior art. However, such methods are linked to high energy consumption and tend to lead to fouling of the surface of the membranes, whereby the service life of the membranes is severely limited.

Other processes involve an acidification step, in which the carboxylic acid is isolated by the addition of a strong acid, while the carboxylic acid salt arising in this case remains in solution (in the case of ammonium sulfate) or in the suspension (in the case of calcium sulfate, the so-called gypsum process). The acidification of diammonium succinate with sulfuric acid thus leads to the formation of ammonium sulfate, a valuable fertilizer.

In order to achieve a separation of the carboxylic acid from the salt, a filtration is carried out in the "gypsum process". It is, however, disadvantageous that the gypsum formed in this case is a waste product and cannot be reutilized.

A further variant for the separation of carboxylic acid and salt is based on a chromatographic separation, e.g. continuous chromatography (SMB, "simulated moving bed"). Due to the high apparatus costs for the chromatographic unit and the high consumption of water as eluent for an efficient separation of salt and acid, there are disadvantages here in terms of process economy.

Owing to the long residence times at high temperature which are required for the evaporation of the water, it is also disadvantageous that a discoloration of the salt generally occurs, which is a result of reactions of the remaining amino acids and the sugar in the salt-containing raffinate stream during the chromatography.

Further steps are required for the recovery of the carboxylic acid or carboxylic anhydrides at the desired purity. Established technologies for this purpose include, for example, ion exchange, nanofiltration, reverse osmosis, extraction, evaporation, distillation, crystallization or recrystallization. Here, the higher the purity requirements for the carboxylic acid, the greater however the complexity linked to the purification and the losses with regard to the yield.

In the case of succinic acid, the most important application here can be seen in the preparation of 1,4-butanediol (BDO), tetrahydrofuran (THF) and γ-butyrolactone (GBL). The last is the starting material for the preparation of 2-pyrrolidone.

BDO, THF and GBL may be prepared by an esterification and hydrogenation process, the DAVY process, starting from maleic anhydride. An intermediate product in this process is dimethyl succinate (DMS). Since this is prepared by an esterification of succinic acid, DMS could be fed into a conventional hydrogenation process for the preparation of BDO, THF or GBL.

In order to be competitive with comparable conventional starting materials, it is necessary to make the process of isolation and purification of the fermented starting materials as efficient as possible. In the case of succinic acid and derivatives thereof, the purification and crystallization of the succinic acid and of the succinic anhydride and the subsequent steps of the dissolution in methanol, esterification and hydrogenation are regarded as weaknesses with regard to efficiency due to the high number of process steps, the energy consumption and the many phase transitions.

Furthermore, it is known that the evaporative crystallization of carboxylic acids, such as succinic acid, is a sensitive process which influences the achievable purity of the crystals and the amount of impurities due to inclusions or sorption effects. It may therefore be necessary to involve a crystallization/recrystallization in order to reduce the impurities to an acceptable degree for the subsequent esterification.

In addition to the desired carboxylic acid, further carboxylic acids are also typically formed as by-products in fermentation processes, which can only be removed with great difficulty by the separation methods mentioned above. The production of succinic acid by fermentation leads at the same time to the formation of, for example, inter alia, acetic acid, lactic acid, fumaric acid and maleic acid as by-products. Depending on the specification of the succinic acid for the esterification and hydrogenation steps for the formation of DMS or even for the subsequent preparation of biopolymers such as polybutylene succinate (PBS), the accumulation of these further carboxylic acids as by-products can lead to formation of undesired alcohols or esters.

A major obstacle for biotechnological processes is the amount of water used. This relates to the energy efficient separation of the product, the large amounts of waste water generated and the requirement for catalytic reactions in an aqueous environment.

To provide efficient processes, depending on the end product, the dissolution behavior of the target components must be taken into account and catalytic processes have to be adjusted.

Therefore, a need exists for a method for preparing and isolating carboxylic esters that ensures a high product purity and minimizes the technical complexity of the individual method steps.

BRIEF DESCRIPTION OF THE FIGURES

FIG. 1 is a schematic diagram of an example method for preparing and isolating carboxylic esters.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

The present disclosure generally concerns methods for preparing and isolating carboxylic esters. Such methods are based on a reaction of a carboxylic acid with an alcohol in an aqueous medium. In some examples, the alcohol may be used both for the esterification and for the precipitation of the salts, preferably ammonium salts, formed in the synthesis.

For instance, some example methods for preparing and isolating carboxylic esters of mono- and dicarboxylic acids, hydroxycarboxylic acids and fatty acids may have the following steps.

a) providing an aqueous solution of at least one carboxylic acid salt,
b) acidifying the aqueous solution with at least one acid to form the free carboxylic acid and a salt of the acid,
c) precipitating the salt by addition of at least one alcohol to the solution,
d) removing the precipitated salt from the solution,
e) esterifying the at least one free carboxylic acid by addition of at least one alcohol and
f) separating the at least one carboxylic ester from the solution.

If a carboxylic acid is referred to below, this is always hereinafter to be understood as meaning at least one carboxylic acid. Therefore, it may also be a mixture of two or more carboxylic acids.

A particular feature of the method according to the invention is that the salts of the acid added in the acidification are removed from the free carboxylic acid in aqueous solution in a simple manner, by addition of an alcohol which causes precipitation of the salt, which can then subsequently be removed by technically simple means from the aqueous solution of the free carboxylic acid.

The following significant advantages over those known from the prior art are linked to the method according to the invention:
preparation of carboxylic esters of high purity
preparation of salts, e.g. ammonium salts, as by-products in high purity
reduction of the risk of biological fouling
energy efficient procedure by reducing the water streams in the process, including the waste water
the method allows recycling of the solvent The salt is preferably an ammonium salt, which can be generated by addition of ammonium hydroxide or ammonium bicarbonate as base. However, it is also possible to provide other salts of the carboxylic acid by adding e.g. sodium, potassium or calcium hydroxide or mixtures thereof as base.

The method according to the invention is particularly suitable for processes in which the carboxylic acid is formed by fermentation. In this case, the carboxylic acid is present in a fermentation broth. The carboxylic acid salt used in step a) is formed by neutralization with a base.

If the carboxylic acid was prepared by fermentation, it is preferred that in a further step, before, during or after step b), the biomass, e.g. cells, cell constituents and proteins, is removed. In this method step, further solids can also be removed for example, if these are present in the fermentation broth. With respect to the separation methods, all standard separation methods known from the prior art are possible. These include, for example, gravimetric separation, centrifugation, micro-, ultra- or nanofiltration and also combinations of the separation methods mentioned.

It is likewise possible that the carboxylic acid was provided by other biotransformation methods.

A further preferred variant of the method according to the invention provides that the solution is concentrated before step b), i.e. before the neutralization of the aqueous solution. This can be accomplished preferably by reverse osmosis or by evaporation of the solution.

With regard to the acid used for the acidification in step b), all protic acids are preferred having a $pK_a$ which is less than the $pK_a$ of the carboxylic acid to be isolated. This protic acid is preferably selected from the group consisting of sulfuric acid, phosphoric acid, nitric acid, salt water, aqua regia, carbonic acid and also mixtures thereof.

It is further preferred that the alcohol added for the precipitation of the salt of the acid is selected from the group of the straight-chain or branched $C_1$-$C_8$-alcohols, particularly methanol, ethanol, propanol, isopropanol, butanol, isobutanol, pentanol, hexanol, heptanol, octanol and mixtures thereof, the group of straight-chain or branched $C_1$-$C_8$-diols, particularly ethylene glycol, propanediol, butanediol, pentanediol, hexanediol, heptanediol, octanediol and mixtures thereof, the group of straight-chain or branched $C_1$-$C_8$-polyols and also mixtures thereof.

The removal of the precipitated salt in step d) can be achieved by any separation methods. Preference is given here to gravimetric separation, centrifugation or combinations thereof.

The salt removed can then preferably be washed and/or dried so that these salts can also be used for further processing.

With regard to the esterification step e), the ratio of alcohol to water is preferably adjusted to from 1:5 to 10:1, preferably from 1:2 to 5:1 and particularly preferably from 1:1 to 5:1.

A catalyst is preferably added in the esterification, which is selected in particular from the group of water-soluble protic acids, in particular sulfuric acid, the group of water-insoluble acids, in particular dodecylbenzenesulfonic acid, the group of lipases such as Novozym 435 or Amano PS the group of solid acids such as Amberlyst 15 or mixtures thereof.

In the case that a water-soluble acid is added as catalyst, it is particularly preferable that said acid in this case is the identical acid that is added in the acidification in step b). In this way, recycling of the acid in the process is enabled which is particularly economical in process terms. In this case, the esterification in step f) is carried out at a temperature of 5° C. to 150° C., preferably 5° C. to 90° C., more preferably 10° C. to 60° C. and particularly preferably 20° C. to 50° C. and/or a pressure of 0.1 to 300 bar, preferably 1 to 300 bar, more preferably 0.1 to 10 bar, even more preferably 0.5 to 5 bar, and particularly preferably 1 to 2 bar.

A further preferred variant provides that the alcohol added in step e) is selected from the group of straight-chain or branched $C_1$-$C_8$-alcohols, particularly methanol, ethanol, propanol, isopropanol, butanol, isobutanol, pentanol, hexanol, heptanol, octanol and mixtures thereof, the group of straight-chain or branched $C_1$-$C_8$-diols, particularly ethylene glycol, propanediol, butanediol, pentanediol, hexanediol, heptanediol, octanediol and mixtures thereof, the group of straight-chain or branched $C_1$-$C_8$-polyols and also mixtures thereof.

It is also particularly preferred with regard to the alcohol used, that the alcohol used for the esterification in step e) is identical to the alcohol added in step c) for the precipitation of the salt of the acid. This also results in a particularly process economic technology since the alcohol is recycled.

It is further preferable that the carboxylic esters are extracted in the esterification in step e). This can preferably be carried out with organic solvents, particularly toluene, chloroform, MTBE or supercritical or subcritical fluids. Particular preference is given here to the use of supercritical $CO_2$. Here also, a process economic recycling of the extraction agent can take place in the process.

Particular preference is given to a variant in which the steps of the precipitation and removal of the precipitated salt of the acid and also of the esterification, i.e. step c), d) and e), are carried out simultaneously.

The separation of the carboxylic esters from the solution provided in step f) can preferably be carried out by distillation or by chromatographic methods. Among the chromatographic methods, particular preference is given in this case to subcritical or supercritical fluid chromatographic methods. In this separation step, if various carboxylic esters are present, these carboxylic esters may also be separated from one another.

In principle, the method according to the invention is suitable for all mono- and dicarboxylic acids, hydroxycarboxylic acids and fatty acids. Mono- and dicarboxylic acids to be mentioned are, for example, formic acid, acetic acid, propionic acid, butyric acid, valeric acid, caproic acid, oxalic acid, malonic acid, succinic acid, glutaric acid, adipic acid, maleic acid, fumaric acid, sebacic acid, dodecanedioic acid, itaconic acid and mixtures thereof. The hydroxycarboxylic acids are preferably selected from the group consisting of malic acid, glycolic acid, mandelic acid, lactic acid, tartronic acid, tartaric acid, citric acid, 3-hydroxypropionic acid, hydroxybutyric acid, mevalonic acid, gallic acid, salicylic acid, hydroxybenzoic acid and mixtures thereof.

With reference now to FIG. 1, a schematic diagram represents an example method according to the present disclosure.

An embodiment of the method according to the invention is shown in the figure, in which the carboxylic acid is initially prepared by fermentation. In this case, a fermentation broth A composed of water, media constituents and sugar is initially charged in which the carboxylic acid is formed. On addition of ammonium hydroxide B, this then leads to the formation of the ammonium salt. In the subsequent separation step, the biomass D, e.g. cells, cell constituents and proteins, is removed. In this step, sulfuric acid can also be added.

The following optional concentration step may then be carried out by evaporation of the aqueous solution of the ammonium salt of the carboxylic acid, whereby water is removed.

Acidification of the aqueous solution takes place in the following step by addition of sulfuric acid. This leads to the formation of the free carboxylic acid and the ammonium salt of the acid. In the salting out step, the ammonium sulfate is then precipitated by addition of an alcohol F. Subsequently, the precipitated ammonium sulfate G is then removed from the solution, for example, by centrifugation or gravimetric separation. Next follows the esterification step in which the free carboxylic acid is esterified by addition of an alcohol F. This step may be combined with extraction by adding an extractant H.

Finally, the product separation step then follows in which the carboxylic ester I is separated from the solution. The waste water J, the alcohol F and optionally the extractant H are further separated from one another. The alcohol F and the extractant H can then be fed again into the process in the relevant method steps, which is particularly economical in process terms.

The method steps of the salting out, the salt removal and the esterification may be carried out in separate units. However, it is likewise possible to combine these steps with one another in subunits as desired or even to carry them out in a single unit.

EXAMPLE 1

Esterification of Aqueous Solutions of Succinic Acid

Succinic acid was reacted with methanol in an aqueous medium. The reaction was carried out in a biphasic medium and was catalyzed with dodecylbenzenesulfonic acid (DBSA) or lipases (Novozym 435, Armano PS). In the presence of DBSA, a homogeneous solution was formed with succinic acid.

The esterification in technical grade methanol proceeded rapidly even at 60° C. and almost quantitatively (Table 1, run 1) while the reaction in a 1:1 mixture of methanol/$H_2O$ as solvent proceeded more slowly. Equilibrium was reached after 24 hours. Dimethyl succinate is in the mixture at ca. 50%. Catalysis with Novozym 435 in alcoholic or aqueous solution was less efficient (runs 5 to 10). A maximum yield of 45% was reached in pure methanol after 48 hours.

TABLE 1

| Run | Catalyst | Slovent | Time [h] | Yield[d] [%] |
|---|---|---|---|---|
| 1 | DBSA[b] | MeOH | 6 | 99 |
| 2 | DBSA[b] | MeOH:$H_2O$ 1:1 | 6 | 40 |
| 3 | DBSA[b] | MeOH:$H_2O$ 1:1 | 24 | 50 |
| 4 | DBSA[b] | MeOH:$H_2O$ 1:1 | 48 | 50 |
| 5 | Novozym 435[c] | MeOH | 6 | 5 |
| 6 | Novozym 435[c] | MeOH | 24 | 23 |
| 7 | Novozym 435[c] | MeOH | 48 | 45 |
| 8 | Novozym 435[c] | MeOH:$H_2O$ 1:1 | 6 | 2 |
| 9 | Novozym 435[c] | MeOH:$H_2O$ 1:1 | 24 | 10 |
| 10 | Novozym 435[c] | MeOH:$H_2O$ 1:1 | 48 | 20 |

[a]3 g succinic acid, 30 mL solvent. 60° C.:
[b]1 g DBSA:
[c]120 mg Nozym 435:
[d]GC yield

EXAMPLE 2

Esterification of Succinic Acid in the Presence of an Organic Solvent

The reaction of succinic acid with methanol in the presence of DBSA was investigated in a biphasic 3-component system (methanol, $H_2O$/organic solvent). The organic solvents used here were chloroform ($CHCl_3$), methyl tert-butyl ether (MTBE) and toluene, which are inert under the reaction conditions.

The reaction mixture with MTBE does not form a biphasic mixture under the reaction conditions. GC analysis showed that the esterification in this system proceeds very slowly (Table 2, run 5).

TABLE 2

| Run | Catalyst | Solvent | Time [h] | Yields [%] org. phase | Yields [%] aqueous phase |
|---|---|---|---|---|---|
| 1 | DBSA[b] | $CHCl_3$ | 7 | 55 | 5 |
| 2 | DBSA[b] | toluene | 7 | 50 | 15 |
| 3 | DBSA[b] | $CHCl_3$ | 20 | 78 | 4 |
| 4 | DBSA[b] | toluene | 20 | 56 | 22 |
| 5 | DBSA[b] | MTBE | 7 | 1 | — |
| 6 | Amberlyst 15 | $CHCl_3$ | 7 | 3 | n.d. |
| 7 | Amberlyst 15 | toluene | 7 | 25 | n.d. |
| 8 | Amberlyst 15 | $CHCl_3$ | 14 | 32 | 1 |
| 9 | Amberlyst 15 | toluene | 14 | 47 | 15 |
| 10 | $H_2SO_4$ | toluene | 7 | 59 | n.d. |
| 11 | $H_2SO_4$ | toluene | 20 | 64 | 16 |

[a]2 g succinic acid, 20 mL solvent, 10 mL MeOH, 10 mL $H_2O$, 65° C.;
[b]0.7 g DBSA;
[c]120 mg Novozym 435; GC yield of DMS.

The two other solvents, $CHCl_3$ and toluene, form an aqueous phase (methanol/$H_2O$) and an organic phase (methanol/organic solvent). More than 50% yield was already found in both mixtures after seven hours (Table 2, runs 1 to 2). The esterification product was distributed between the two phases.

The GC yields of product, which were calculated from the concentrations of dimethyl succinate (DMS) in organic and aqueous phases, are summarized in Table 2. The product distribution between organic and aqueous medium was better in chloroform than in toluene. The free acid and monomethyl succinate (MMS) were also effectively extracted into the organic phase.

Toluene was distinctly more selective and dissolves practically no succinic acid and MMS. The best yield of 78% was achieved after 20 hours at 65° C. using $CHCl_3$ and DBSA as catalyst (run 3).

The use of other Brønsted acids, namely Amberlyst 15 and sulfuric acid, was likewise investigated. Both catalysts were able to catalyze the esterification. In the case of the strongly acidic cation resin Amberlyst 15, a 3-phase system forms consisting of resin/org. phase/aqueous phase, and therefore the yields are highly dependent on the stirring efficiency (runs 6-9).

The use of sulfuric acid is likewise possible (runs 10-11). Here, the acid remained practically exclusively in the aqueous phase.

EXAMPLE 3

Precipitation and Isolation of Ammonium Sulfate (Inventive Steps c and d)

5 ml of a 10 g/L concentrated diammonium succinate solution were acidified to pH 2.2 with sulfuric acid.

The aqueous solution of ammonium sulfate and succinic acid generated in this case was mixed at room temperature in a volumetric ratio of one part of this aqueous solution to 4 parts methanol. The residue precipitated here was isolated with a yield by mass of 70% (based on the theoretical amount of ammonium sulfate generated) and was investigated by $^1H$—, $^{13}C$-NMR spectroscopy and elemental analysis.

The analysis of the residue resulted in practically pure ammonium sulfate having ca. 0.5% impurities of succinic acid.

The result of two elemental analyses was in this case:

C=0.3816% H=6.046% N=21.35% S=23.30%

C=0.2327% H=6.271% N=21.48% S=24.21%

Analysis of the evaporated mother liquor gave a mixture of succinic acid and low residues of ammonium sulfate (ca. 15%).

The result of two elemental analyses was in this case:

C=31.07% H=4.931% N=3.471% S=2.521%

C=31.73% H=5.038% N=3.171% S=3.684%

What is claimed is:

1. A method for preparing and isolating carboxylic esters of mono- and dicarboxylic acids, hydroxycarboxylic acids, and fatty acids, the method comprising:
    providing an aqueous solution of at least one salt of at least one carboxylic acid;
    acidifying the aqueous solution with at least one acid to form a free carboxylic acid and a salt of said at least one acid;
    precipitating the salt of said at least one acid, formed in said acidifying step, by adding at least one alcohol to the aqueous solution;
    removing the precipitated salt from the aqueous solution;
    esterifying the at least one free carboxylic acid by adding at least one alcohol; and
    separating at least one carboxylic ester from the aqueous solution.

2. The method of claim 1 wherein the at least one salt of the aqueous solution consists of ammonium salt, calcium salt, potassium salt, sodium salt, or a combination thereof.

3. The method of claim 1 further comprising preparing the at least one carboxylic acid of the aqueous solution by fermentation or another biotransformation process, wherein the aqueous solution comprises a fermentation broth comprising biomass present as a suspension, wherein the carboxylic acid salt of the aqueous solution is prepared by neutralization with a base.

4. The method of claim 3 further comprising removing the biomass including any cells and solids present in the aqueous solution directly before, during, or directly after acidifying the aqueous solution, wherein the removing occurs by way of gravimetric separation, centrifugation, microfiltration, ultrafiltration, nanofiltration, and/or any combination thereof.

5. The method of claim 1 further comprising concentrating the aqueous solution by reverse osmosis or evaporation before acidifying.

6. The method of claim 1 wherein the at least one acid used to acidify the aqueous solution has a pKa value less than a pKa value of the carboxylic acid to be isolated and consists of sulfuric acid, phosphoric acid, nitric acid, salt water, aqua regia, carbonic acid, or combinations thereof.

7. The method of claim 1, wherein the at least one alcohol added to the aqueous solution is one or more of:
    a straight-chain or branched $C_1$-$C_8$-alcohol, comprising one or more of methanol, ethanol, propanol, isopropanol, butanol, isobutanol, pentanol, hexanol, heptanol, octanol, and combinations thereof;

a straight-chain or branched $C_1$-$C_8$-diol, comprising one or more of ethylene glycol, propanediol, butanediol, pentanediol, hexanediol, heptanediol, octanediol, and combinations thereof; or a straight-chain or branched $C_1$-$C_8$-polyol.

8. The method of claim 1 wherein removing the precipitated salt from the aqueous solution comprises using a separation process involving gravimetric separation, centrifugation, or combinations thereof.

9. The method of claim 1 further comprising at least one of washing or drying the precipitated salt that is removed from the aqueous solution.

10. The method of claim 1, further comprising:
adjusting a ratio of alcohol to water in the esterification from 1:5 to 10:1.

11. The method of claim 1, further comprising:
during said esterifying step, further adding a catalyst that is one or more of:
a water-soluble protic acid,
a water-insoluble acid,
a lipase, or
a solid acid.

12. The method of claim 1 wherein the esterifying is performed at a temperature of between 5-150 degrees Celsius and/or a pressure of 0.1-10 bar.

13. The method of claim 1 wherein the esterifying comprises adding CO2 as a catalyst.

14. The method of claim 1 wherein the esterifying is performed at a temperature of between 5-90 degrees Celsius and/or a pressure of 1-300 bar.

15. The method of claim 14 wherein the at least one acid used to acidify the aqueous solution is a water-soluble acid and is recyclable in the method.

16. The method of claim 1, wherein the at least one alcohol used in the esterifying is one or more of:
a straight-chain or branched $C_1$-C8-alcohol, comprising one or more of methanol, ethanol, propanol, isopropanol, butanol, isobutanol, pentanol, hexanol, heptanol, octanol, and combinations thereof;
a straight-chain or branched $C_1$-$C_8$ diol, comprising one or more of ethylene glycol, propanediol, butanediol, pentanediol, hexanediol, heptanediol, octanediol, and combinations thereof; or
a straight-chain or branched $C_1$-$C_8$-polyol.

17. The method of claim 16 wherein the at least one alcohol used in the esterifying is identical to the at least one alcohol used in the precipitating such that the at least one alcohol is recyclable in the method.

18. The method of claim 1 wherein the esterifying comprises extracting carboxylic esters with at least one organic solvent.

19. The method of claim 1 wherein the precipitating, the removing the precipitated salt, and the esterifying occur simultaneously.

20. The method of claim 1 wherein the separating the at least one carboxylic ester is effected by distillation, subcritical fluid chromatography, or supercritical fluid chromatography.

21. The method of claim 1 further comprising converting the at least one carboxylic ester into the free carboxylic acid after separating the at least one carboxylic ester.

22. The method of claim 1, wherein the mono- or dicarboxylic acids are one or more of formic acid, acetic acid, propionic acid, butyric acid, valeric acid, caproic acid, oxalic acid, malonic acid, succinic acid, glutaric acid, adipic acid, maleic acid, fumaric acid, sebacic acid, dodecanedioic acid, or itaconic acid, and/or the hydroxycarboxylic acids are one or more of malic acid, glycolic acid, mandelic acid, lactic acid, tartronic acid, tartaric acid, citric acid, 3-hydroxypropionic acid, hydroxybutyric acid, mevalonic acid, gallic acid, salicylic acid, or hydroxybenzoic acid.

* * * * *